United States Patent [19]

Youssefyeh et al.

[11] 4,239,887

[45] Dec. 16, 1980

[54] PYRIDOTHIENOTRIAZINES

[75] Inventors: Raymond D. Youssefyeh, Tarrytown, N.Y.; Jeffrey D. Wilson, Durham, N.C.

[73] Assignee: USV Pharmaceutical Corporation, Tuckahoe, N.Y.

[21] Appl. No.: 89,853

[22] Filed: Oct. 31, 1979

[51] Int. Cl.³ ............................................ C07D 513/14
[52] U.S. Cl. ................................... 544/184; 546/114; 424/249
[58] Field of Search ........................................ 544/184

[56] References Cited

PUBLICATIONS

Chemical Abstracts, vol. 83, Item 10008, (1975) Abstracting Schneller et al., in "Heterocycles", vol. 3, No. 2, pp. 135–138 (1975).

*Primary Examiner*—Henry R. Jiles
*Assistant Examiner*—Robert T. Bond
*Attorney, Agent, or Firm*—Leon E. Tenenbaum

[57] ABSTRACT

New pyridothienotriazines are described. These compounds are useful as anti-allergic reagents.

26 Claims, No Drawings

PYRIDOTHIENOTRIAZINES

This invention relates to new anti-allergy agents and more particularly to certain new pyridothienotriazines possessing useful anti-allergy activity.

4-Hydroxy-pyrido[3',2':4,5]thieno[3,2-d]-1,2,3-triazine, together with the corresponding pyrazinothieno and benzothieno compounds, is described by A. W. Schneller and F. U. Clough, Heterocycles 3, 135 (1975). Derivatives of the 4-hydroxy benzothienotriazine are described by J. R. Beck and Y. A. Yahner, J. Org. Chem. 41, 1733 (1976).

It has now been surprisingly discovered that certain new pyridothienotriazines and pyridothienotriazinones have significant oral anti-allergy activity whereas the known 4-hydroxy pyrido[3',2':4,5]thieno[3,2-d]-1,2,3-triazine is essentially inactive when tested for anti-allergy activity utilizing standard tests employed for determining such activity.

The new pyridothienotriazines and pyridothienotriazinones of this invention are substituted in the pyridine and/or triazine rings with a variety of substituents such as alkyl, alkoxy, alkynyloxy, alkenyloxy, hydroxy, nitro, halo, carboxy, carbalkoxy, cyano, trifluoromethyl, alkoxyalkoxy, aralkyl, aralkyloxyalkoxy, aralkyloxy, hydrazino, amino, alkylamino, alkanoylamino, alkenyl, alkynyl, aryl, alkaryl and alkanoyloxy. The number of substituents on the pyridine ring can range from one to three, but usually not more than two substituents are present in the instant new compounds. There should be at least one substituent on the pyridine ring.

The present new compounds are represented by the following formulae:

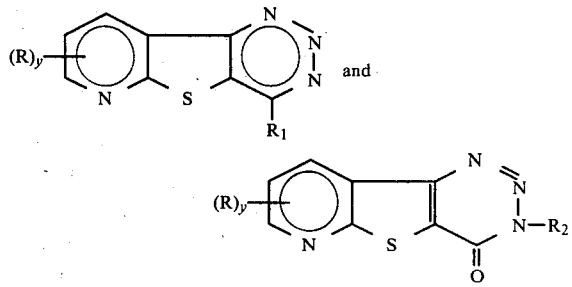

wherein,

R and $R_1$ each are hydrogen, alkyl, alkenyl, alkynyl, aryl, aralkyl, halogen, alkoxy, alkenyloxy, alkynyloxy, cyano, hydroxy, acyloxy, amino, alkylamino, alkanoylamino, carbalkoxyamino, carboxy, carbalkoxy, or trihaloalkyl; y is an integer from 1 to 3; and $R_2$ is alkyl, alkenyl, alkynyl, aryl, acyl, aralkyl or carbalkoxy, provided that R is other than hydrogen when $R_1$ is hydroxyl. The total number of carbon atoms in each such hydrocarbyl substituent can range up to about 10.

The preferred compounds are those in which the hydrocarbyl radicals representative of R, $R_1$ and $R_2$ contain up to 7 carbon atoms when aliphatic and up to 10 carbon atoms when aromatic, e.g., phenyl and naphthyl. The aryl, aralkyl and alkaryl radicals also are intended to include the known heterocyclic rings such as furan, thiophene, thiazole, pyridine, pyrimidine, piperidine, oxazoles, and the like, as well as benzo-heterocyclics such as benzothiophene and benzofuran.

The new compounds of this invention can be prepared by art-recognized procedures from 2-mercapto-3-cyanopyridine employing the reaction sequence, as follows:

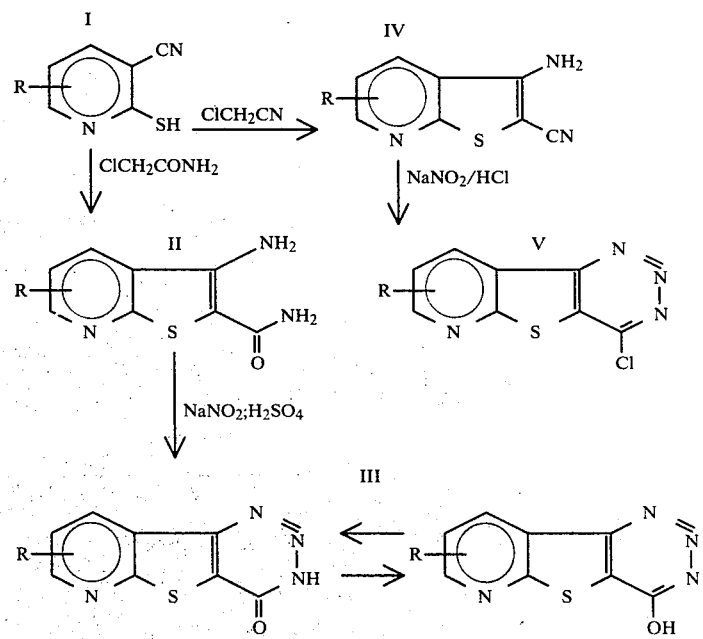

The reaction sequences provide compounds of Formula III which exist as a mixture of keto and enol forms. Compounds of Formula III can be further reacted with suitable halo compounds to introduce $R_2$ on the cyclic amide nitrogen of the keto forms. The 4-chloro compound of Formula V can be converted to various 4-substituted compounds by reaction with suitable compounds to introduce R₁ substituents, e.g., with dimethylamine to introduce the dimethylamino group or with thiourea to introduce a mercapto group. Various other groups represented by (R)ᵧ can be introduced by similar procedures known in the art, as for example, reduction of a nitro group to an amino group and hydrolysis of a cyano group to an amide or carboxyl group.

Using the reaction sequences described, a wide variety of pyridothienotriazines can be prepared as shown in the following table:

| (R)$_y$ | R$_1$ | R$_2$ |
|---|---|---|
| 7-Me | OEt | — |
| 7-C$_6$H$_5$ | — | Et |
| 7-C$_6$H$_5$ | OEt | — |
| 7,9-diMe | NH$_2$ | — |
| 7-OMe | — | COCH$_3$ |
| 7-CN | — | C$_6$H$_5$CH$_2$ |
| 7-CO$_2$Me | — | —CH$_2$—CH=CH$_2$ |
| 7-CF$_3$ | NHNH$_2$ | — |
| 7,9-diOMe | OCH$_2$CH$_2$OEt | — |
| 7-C$_6$H$_5$CH$_2$ | H | — |
| 7-Me$_2$N | Cl | — |
| 7-NO$_2$ | — | COOEt |
| 7-NH$_2$ | Cl | — |
| 7-C$_3$H$_7$ | Cl | — |
| 7-CH$_3$—9-NO$_2$ | Cl | — |
| 7-C$_6$H$_5$CH$_2$ | H | — |
| 7-Bu | H | — |
| 7-CF$_3$ | H | — |
| 7-CH$_3$ | H | — |
| 7-SCH$_3$ | H | — |

The present new heterocyclic esters are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new esters. Therefore, all acid salts of the present new esters are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic esters are particularly useful as anti-allergy agents, acting via inhibition of mediator release. These esters are active orally in the passive cutaneous anaphylaxis (PCA) screen; and/or inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

3-Amino-2-cyano-6-methylthieno[2,3-b]pyridine

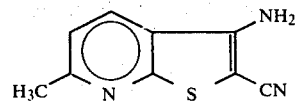

To a solution of 7.5 g. (0.05 mole) of 2-mercapto-3-cyano-6-methylpyridine in 200 ml. of MeOH was added 5.4 g. (0.1 M) sodium methoxide. Stirring was continued until all dissolved. 8.0 g. (0.1 M) of chloroacetonitrile in 20 ml. methanol was then added and the mixture was refluxed for 6 hours. After removal of the solvent, the residue was diluted with water and filtered. The crude product was crystallized from methanol, m.p. 241°–242° C. (Offin No. 2,241,717 in 3/4/74 reported m.p. 241°–243°).

In the same manner, the following 2-substituted derivatives of 3-amino-6-methylthieno[2,3-b]pyridine were prepared:

CONH$_2$: m.p. 237°–238° C.
CO$_2$Et: m.p. 196°–198° C.
COCH$_3$: m.p. 176°–177° C.
COC$_6$H$_5$: m.p. 193°–196° C.

Similarly, the use of 2-mercapto-3-cyano-pyridines having the following substituents:
6-methoxy
6-cyano
6-trifluoromethyl
6-benzyl
6-nitro
gives the corresponding 2-cyano-3-amino-6-substituted-thieno[2,3-b]pyridines, respectively.

EXAMPLE 2

4-Hydroxy-7-methylpyrido[3',2':4,5]thieno[3,2-d]-1,2,3-triazine

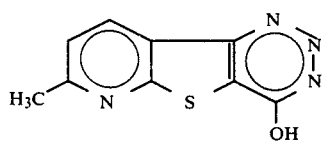

To a cold solution of 2.7 g. (0.04 M) sodium nitrite in 65 ml. concentrated sulfuric acid was slowly added a suspension of 8 g. (0.039 M) of 3-amino-2-carboxamido-6-methylthieno-[2,3-b]pyridine in 250 ml. acetic acid. Stirring was continued for one additional hour. It was then filtered and the filtrate was poured on ice. The crude product was filtered, dissolved in 5% sodium hydroxide, treated with charcoal and acidified with HOAC giving 4-hydroxy-7-methyl-pyrido[3,2':4,5]-thieno[3,2-d]-1,2,3-triazine, m.p. 215°–216° C.

In the same manner, diazotization of the following 6-substituted-3-amino-2-carboxamido-6-substituted-thieno[2,3-b]pyridines gives the corresponding 7-substituted-4-hydroxy-pyrido[3',2':4,5]-thieno[3,2-d]-1,2,3-triazines, respectively.
6-methoxy
6-cyano
6-trifluoromethyl
6-benzyl
6-nitro

EXAMPLE 3

4-Hydroxy-7,9-dimethylpyrido[3',2':4,5]thieno[3,2-d]-1,2,3-triazine

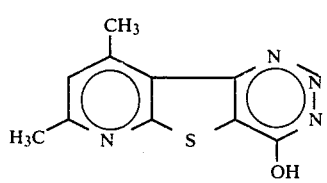

This compound was prepared from appropriate reactants by the procedure described in EXAMPLE 2, m.p. 215°–216° C.

EXAMPLE 4

4-Hydroxy-7-phenylpyrido[3',2':4,5]thieno[3,2-d]-1,2,3-triazine

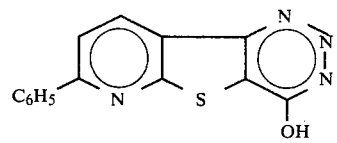

This compound was prepared from appropriate reactants by the procedure described in Example 2, m.p.>280° C.

EXAMPLE 5

4-Chloro-7-methylpyrido[3',2':4,5]thieno[3,2-d]-1,2,3-triazine

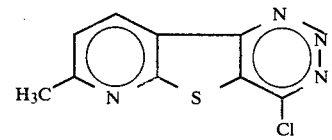

To a cold solution of 4.2 g. (0.022 M) of 3-amino-2-cyano-6-methylthieno[2,3-b]pyridine in 30 ml. conc. HCl and 30 ml. HOAC was added a solution of 1.9 g. (0.028 M) of NaNO$_2$ in 20 ml. of H$_2$O. After completion of addition, the ice bath was removed and stirring continued for 2 more hours. The mixture was then poured on ice water and filtered. The crude product was recrystallized from methanol, m.p. 188°–189° C.

In the same manner, diazotization of the following 6-substituted-3-amino-2-cyano-6-substituted-thieno[2,3-b]-pyridines gives the corresponding 7-substituted-4-chloropyrido-[3',2':4,5]thieno[3,2-d]-1,2,3-triazines, respectively.
6-methoxy
6-cyano
6-trifluoromethyl
6-benzyl
6-nitro

EXAMPLE 6

4-Methylamino-7-methylpyrido[3',2':4,5]thieno[3,2-d]-1,2,3-triazine

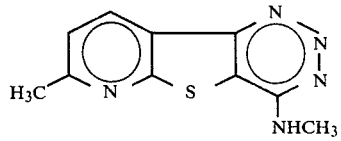

To a solution of 5 g. (0.02 M) of 4-chloro-7-methylpyrido[3',2':4,5]thieno[3,2-d]-1,2,3-triazine in 500 ml. of ethanol at 70° C. was bubbled methylamine gas for one hour. After cooling to room temperature, the mixture was evaporated to dryness, diluted with water and filtered. Crystallization of the crude product from acetic acid-ether gave pure product, m.p. 256°–260° C.

In the same manner, the following 4-substituted derivatives of 7-methylpyrido[3',2':4,5]thieno[3,2-d]-1,2,3-triazine were prepared by use of the appropriate amine or alcohol:

| | |
|---|---|
| NH$_2$ | m.p. 300° C. |
| NHNH$_2$ | m.p. 218 decomposition |
| NHNHCO$_2$Me | m.p. 210–211° C. |
| NHN=C(CH$_3$)(CH$_3$) | m.p. 234–236° C. |
| OEt | m.p. 171–173° C. |
| OMe | m.p. 190–191° C. |
| OCH$_2$CH$_2$OEt | m.p. 125–126° C. |

EXAMPLE 7

4-Mercapto-7-methylpyrido[3',2':4,5]thieno[3,2-d]-1,2,3-triazine

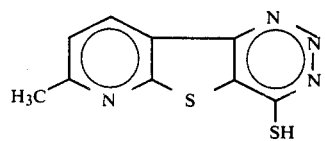

A mixture of 7 g. (0.03 M) of 4-chloro-7-methylpyrido[3',2':4,5]thieno[3,2-d]-1,2,3-triazine, and 7 g. (0.09 M) of thiourea in 350 ml. ethanol was refluxed for 2 hours. It was then cooled and filtered. The crude product was dissolved in 5% NaOH, and treated with charcoal and filtered. Acidification with HOAC followed by filtration yielded yellow solid, m.p. 205°–208° C.

EXAMPLE 8

4-Methylthio-7-methylpyrido[3',2':4,5]thieno[3,2-d]-1,2,3-triazine

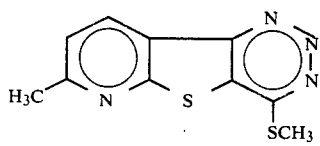

To a solution of 5 g. (0.02 M) of the thiol in 400 ml. of 5% NaOH was added 5 ml. of methyl iodide and the mixture was stirred for two hours. The solid precipitate which formed was collected and crystallized from ethanol, m.p. 197°–198° C.

EXAMPLE 9

3,7-Dimethylpyrido[3',2':4,5]thieno[3,2-d]-1,2,3-triazine-4-one

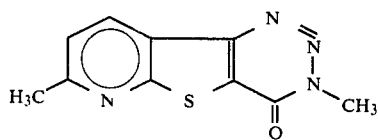

To a mixture of 6 g. (0.028 M) of 4-hydroxy-7-methylpyrido[3',2':4,5]thieno[3,2-d]-1,2,3-triazine, 12 g. of K$_2$CO$_3$ in 150 ml. DMF at 75° C. was added 6 ml. methyl iodide and stirring at this temperature was continued for 3 hours. The mixture was then diluted with water and the precipitated product was collected by filtration. Crystallization with chloroform gave m.p. 169°–171° C.

EXAMPLE 10

3-Ethyl-7-methylpyrido[3',2':4,5]thieno[3,2-d]-1,2,3-triazine-4-one

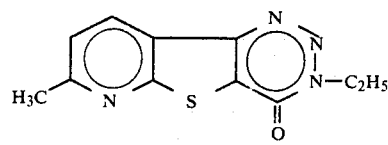

In the same way as described in Example 9, use of ethyl iodide gave this compound, m.p. 165°–167° C.

EXAMPLE 11

7-Methylpyrido[3',2':4,5]thieno[3,2-d]-1,2,3-triazine

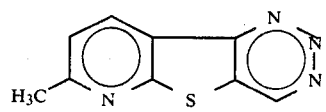

A mixture of 8.3 g. (0.036 M) 4-hydrazino-7-methylpyrido[3',2':4,5]thieno[3,2-d]-1,2,3-triazine and 8.5 g. (0.039 M) mercuric oxide in 500 ml. water was stirred at 50° C. for 24 hours. It was then filtered. The crude product was extracted with 600 ml. dichloromethane, treated with charcoal and concentrated to 200 ml. Filtration and recrystallization from dichloromethane-ether gave product of m.p. 248°–250° C.

In the same way as described in EXAMPLES 5, 6 and 11, 3-amino-2-cyano-4,6-dimethylthieno[2,3-b]pyridine and 3-amino-2-cyano-6-phenylthieno[2,3-b]pyridine give 7,9-dimethylpyrido-[3',2':4,5]thieno[3,2-d]-1,2,3-triazine and 7-phenylpyrido-[3',2':4,5]thieno[3,2-d]-1,2,3-triazine, respectively.

In the same manner as described in Examples 6 and 11, the following 7-substituted-4-chloropyrido[3',2':4,5]thieno-[3,2-d]-1,2,3-triazines were reacted with hydrazine followed by mercuric oxide to give the following 7-substituted-pyrido-[3',2':4,5]thieno[2,3-d]-1,2,3-triazines.

7-methoxy
7-cyano
7-trifluoromethyl
7-benzyl
7-nitro

The compounds of this invention have potent activity in inhibiting the formation of a wheal when screened according to the Rat Passive Cutaneous Anaphylaxis Screen as is described by I. Mota, Life Sciences, 7, 465 (1963) and Z. Ovary, et al., Proceedings of Society of Experimental Biology and Medicine, 81, 584 (1952).

The activities of the most potent compounds of this invention are given in the following table. The activities are given as ED$_{50}$ values, which are the doses required to give 50% reductions in wheal size.

| (R)$_y$ | R$_1$ | ED$_{50}$, mg/kg, p.o. |
|---|---|---|
| 7-CH$_3$ | OH | 6.0 |
| 7,9-diCH$_3$ | OH | 5.6 |
| 7-CH$_3$ | H | 1.0 |

-continued

| 7-phenyl | OH | 0.74 |

In contrast to the above, the known compound wherein $(R)_y$ is hydrogen and $R_1$ is OH gives only 31% inhibition of wheal size when tested at 25 mg/kg, p.o.

This property of inhibiting the formation of wheal would make these compounds useful in the treatment of asthma and other allergic reactions.

What is claimed is:

1. A compound of the formula

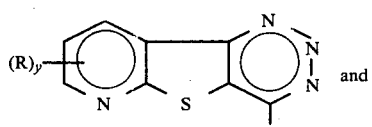

and

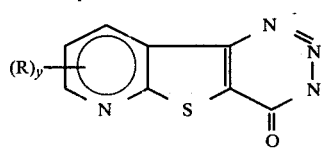

wherein R and $R_1$ are independently hydrogen, alkyl, alkenyl, alkynyl, aryl, aralkyl, halogen, alkoxy, alkenyloxy, alkynyloxy, alkylamino, alkanoylamino, carbalkoxy, carbalkoxyamino, alkanoyloxy or trihaloalkyl; y is an integer from 1 to 3; and $R_2$ is alkyl, alkenyl, alkynyl, aryl, aralkyl, alkanoyl or carbalkoxy; wherein the alkyl, alkenyl, alkynyl, alkoxy, alkanoyl and carbalkoxy groups contain up to 7 carbon atoms and the aryl and aralkyl groups contain up to 10 carbon atoms, with the proviso that when $R_1$ is hydroxy, R is not hydrogen.

2. A compound of the formula

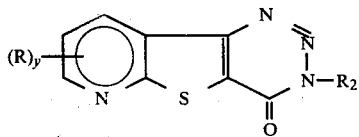

wherein R is hydrogen, alkyl, alkenyl, alkynyl, aryl, aralkyl, halogen, alkoxy, alkenyloxy, alkynyloxy, alkylamino, alkanoylamino, carbalkoxy, carbalkoxyamino, alkanoyloxy, or trihaloalkyl; y is an integer from 1 to 3; and $R_2$ is alkyl, alkenyl, alkynyl, aryl, aralkyl, or carbalkoxy, wherein the alkyl, alkenyl, alkynyl, alkoxy, alkanoyl and carbalkoxy groups contain up to 7 carbon atoms and the aryl and aralkyl groups contain up to 10 carbon atoms.

3. A compound of the formula

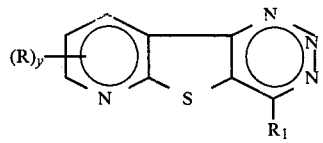

wherein R and $R_1$ are independently hydrogen, alkyl, alkenyl, alkynyl, aryl, aralkyl, halogen, alkoxy, alkenyloxy, alkynyloxy, alkylamino, alkanoylamino, carbalkoxy, carbalkoxyamino, alkanoyloxy, or trihaloalkyl; and y is an integer from 1 to 3; wherein the alkyl, alkenyl, alkynyl, alkoxy, alkanoyl, and carbalkoxy groups contain up to 7 carbon atoms, with the proviso that when $R_1$ is hydroxy, R is not hydrogen.

4. The compound according to claim 2 wherein R and $R_2$ are each lower alkyl.

5. The compound according to claim 2 wherein R is lower alkyl and $R_2$ is aralkyl.

6. The compound according to claim 3 wherein R is aryl and $R_1$ is hydroxy.

7. The compound according to claim 3 wherein R is alkyl and $R_1$ is hydroxy.

8. The compound according to claim 3 wherein R is aryl and $R_1$ is hydrogen.

9. The compound according to claim 3 wherein R is alkyl and $R_1$ is hydrogen.

10. The compound according to claim 3 wherein R is lower alkyl and $R_1$ is chloro.

11. The compound according to claim 3 wherein R is lower alkyl and $R_1$ is alkoxy.

12. The compound according to claim 3 wherein R is lower alkyl and $R_1$ is amino.

13. The compound according to claim 3 wherein R is lower alkyl and $R_1$ is mercapto.

14. 7-Methylpyrido[3',2':4,5]thieno[3,2-d]-1,2,3-triazine.

15. 4-Hydroxy-7,9-dimethylpyrido[3',2':4,5]thieno[3,2-d]-1,2,3-triazine.

16. 4-Hydroxy-7-phenylpyrido[3',2':4,5]thieno[3,2-d]-1,2,3-triazine.

17. 4-Chloro-7-methylpyrido[3',2':4,5]thieno[3,2-d]-1,2,3-triazine.

18. 4-Methylamino-7-methylpyrido[3',2':4,5]thieno[3,2-d]-1,2,3-triazine.

19. 4-Mercapto-7-methylpyrido[3',2':4,5]thieno[3,2-d]-1,2,3-triazine.

20. 4-Methylthio-7-methylpyrido[3',2':4,5]thieno[3,2-d]-1,2,3-triazine.

21. 3,7-Dimethylpyrido[3',2':4,5]thieno[3,2-d]-1,2,3-triazine-4(3H)one.

22. 4-Hydroxy-7-methylpyrido[3',2':4,5]thieno[3,2-d]-1,2,3-triazine.

23. 4-Hydrazino-7-methylpyrido[3',2':4,5]thieno[3,2-d]-1,2,3-triazine.

24. An acid addition salt of the compound of claim 1.

25. An acid addition salt of the compound of claim 2.

26. An acid addition salt of the compound of claim 3.

* * * * *